United States Patent [19]

Martini et al.

[11] 4,141,791

[45] Feb. 27, 1979

[54] MILK COAGULATING MICROBIAL ENZYME

[76] Inventors: Alessandro Martini, Via della Barca, Frazione Ponte S. Giovanni(Prov. Perugia); Federico Federici, Via Vespucci, Frazione Ferro di Cavallo(Prov. Perugia); Benito Argenti, Via Tiberina Nord, 1352, Frazione Pieve Pagliaccia (Prov. Perugia), all of Italy

[21] Appl. No.: 755,389

[22] Filed: Dec. 27, 1976

[51] Int. Cl.$^2$ .......................... C07G 7/02; A23C 19/02
[52] U.S. Cl. ..................................... 195/66 R; 195/62; 426/36; 426/42; 426/63
[58] Field of Search ....................... 426/38, 42, 63, 36; 195/62, 66 R

[56] References Cited

U.S. PATENT DOCUMENTS 3,607,655   9/1971   Mukai et al. ...................... 195/66 X

OTHER PUBLICATIONS

Yoshino, et al., Milk Coagulating Activity of Protease Produced by *Candida Lipolytica*, Chemical Abstracts, vol. 78, 1973, (p. 346, 722810v).

*Primary Examiner*—David M. Naff
*Attorney, Agent, or Firm*—Guido Modiano; Albert Josif

[57] ABSTRACT

A novel milk coagulating enzyme is produced by cultivating a yeast of the group *Cryptococcus albidus* and its variants *aerius* and *diffluens* on a culture medium containing assimilable carbon, nitrogen and trace nutrients at a temperature between 15° C. and 40° C. under aerobic conditions, and at a pH of between 3.0 and 8.0. The enzyme is recovered from the culture medium, for example, by salting-out, dialyzed and freeze-dried. The preparations obtained are characterized by high milk-clotting activity with very low proteolytic activity.

4 Claims, No Drawings

MILK COAGULATING MICROBIAL ENZYME

BACKGROUND OF THE INVENTION

The present invention relates to a novel milk coagulating microbial enzyme and to a method for its production.

Rennet, an enzyme that is obtained from the fourth stomach of sucking calves, is a very active milk coagulating agent. For this reason it has been and is now widely used for cheese-making. However, the increasing difficulties in obtaining raw material for rennet extraction, originated the actual search for substitutes of different origins.

Generally, proteolytic enzymes (proteases), whether of animal (pepsin, chemotrypsin, trypsin, catepsin, etc.) or plant origin (papain, ficin, bromelain, etc.) are characterized by coagulating activity. Furthermore, proteases produced by bacteria are also known as, for example, those elaborated by *Pseudomonas fluorescens*, *Bacillus subtilis* and *Serratia marcescens*. Some of these enzymes are able to cause a rennet-like coagulation in milk. However, their extremely high proteolytic activity impedes their use in cheese-making. In effect, the enzymes produced by these microorganisms cause the development of off-flavors in cheese, affect the consistency of the product, and develop excessively high amounts of acids by the very reason of their characteristically excessive proteolytic activity.

Furthermore it is also known that milk-clotting enzymes can be found in cultural broths of some fungi belonging to the genera Mucor (*Mucor pusillus, Mucor rouxii* and *Mucor miehei*) and Endothia (*Endothia parasitica*). Microbial rennet produced by some of the above mentioned species are presently used in cheese-making because of their reasonably low proteolytic activity.

However, it is not so far known that a milk-clotting enzyme advantageously utilizable on a commercial scale, can be found in the cultural broths of a group of microbes which are classified with the name of "yeasts" or Blastomycetes.

From a botanical standpoint it is very difficult to include yeasts in a single homogeneous group: they belong to the division Thallophyta of the Plant kingdom, lack chlorophyll, possess a definite cell wall and a nucleus, and lack any means of locomotion. These properties fit only one of the ten subdivisions of Tallophyta, namely the phylum Eumycophyta, or true fungi. However, botanists consider yeasts as rather primitive or degenerated forms of Eumycophyta. Their structural simplicity, almost total lack of mycelium, the formation of the ascus independently of the action of an ascogenous hypha system, and the total absence of ascocarps, and above all their monocellular life conditions, all make their systematic classification a difficult task.

SUMMARY OF THE INVENTION

A primary object of this invention is the production on a commercial scale of a novel, low-cost, microbial milk coagulating enzyme, characterized by high milk-clotting activity and almost completely deprived of protease activity.

An additional object of this invention is to provide a method for the production of the aforementioned milk-clotting enzyme, hereinafter called blastomycetal, by cultivating on a suitable medium a selected yeast.

Still another object of the invention is to provide a method of recovering the blastomycetal rennet from the cultural broth and of preparing it in its final form.

It is a further object of the invention to make available a novel rennet allowing the production of cheese on an industrial scale.

These and other objects, such as will become more apparent hereinafter, are achieved by a method of preparing a milk coagulating enzyme, according to the invention, characterized in that it comprises the steps of cultivating a yeast selected from the group consisting of genus Cryptococcus, genus Candida, genus Torulopsis, genus Rhodotorula, genus Kluyveromyces, and their varieties and the natural and artificially induced mutants thereof, on a nutrient medium containing at least one assimilable carbon source, at least one source of assimilable nitrogen and inorganic salts, to recover a culture broth containing a substance capable of coagulating milk, and extracting said substance from said culture liquid.

DESCRIPTION OF THE PREFERRED EMBODIMENTS

According to our studies conducted on the metabolic products of a group of microorganisms systematically referred to as yeasts or Blastomycetes, it has been found that it is possible to obtain a microbial milk-clotting enzyme practically deprived of protease activity by using these yeasts, their varieties and natural or artificially induced mutants, i.e. which have most of the characteristic properties of the related Blastomycetal species. The yeasts capable of producing the novel milk coagulating enzyme, termed Blastomycetal or yeast rennet, characterized by an elevated milk-clotting activity and by a remarkably low protease activity, include the species *Cryptococcus albidus* and other species belonging to the genus Cryptococcus, genus Candida, genus Torulopsis, genus Rhodotorula, their variants and the natural and artificially induced mutants thereof.

As already mentioned, it is known that several fungi such as *Endothia parasitica, Mucor rouxii, Mucor pusillus* and *Mucor miehei* are capable to produce on suitable culture media a milk coagulating enzyme. However, it was not known that *Cryptococcus albidus* and other aforementioned species of yeasts secrete in their culture media a milk coagulating enzyme which can be put to practical use in the dairy industry with much improved results due to its very low protease activity.

According to this invention, some yeast species of the genus Cryptococcus, genus Candida, genus Torulopsis, genus Rhodotorula, genus Kluyveromyces, their varieties, and natural and artificially induced mutants, can be used as the true fungi aforementioned to produce milk-clotting enzymes. As species belonging to the aforementioned yeasts can be mentioned: *Cryptococcus albidus, Cryptococcus albidus* var. *aerius, Cryptococcus albidus* var. *diffluens, Rhodotorula glutinis, Torulopsis aeria, Candida lipolytica, Kluyveromyces aestuarii*.

Since the property of producing milk-clotting enzymes is characteristic of numerous yeast species belonging to several different genera, a detailed description of each will be omitted. However, an exhaustive enumeration of the characteristic properties of the foregoing genera and species of yeasts appears in the following monographs:

"The Yeasts. A Taxonomic Study" by Lodder, J. and Kreger van Rij, N.J.W. North-Holland Publishing Company, Amsterdam, 1952.

"The Yeasts, A Taxonomic Study" edited by Lodder, J., North-Holland Publishing Company, Amsterdam, 1970.

The method will be now described by which a yeast selected from the group including *Cryptococcus albidus* and the species above mentioned, belonging to the genus Cryptococcus, genus Candida, genus Torulopsis, genus Rhodotorula, genus Kluyveromyces, their variants, and the natural and artificially induced mutants, is cultivated in order to produce "yeast rennet" in its medium, and by which the same enzyme is concentrated and partially purified.

According to the invention, the culture medium to be used for growing the yeasts can be any suitable artificial or natural medium containing at least a carbon source, a nitrogen source and inorganic salts.

As the carbon monosaccharides, disaccharides and polysaccharides which are assimilable by the instant yeasts such as glucose, sucrose, lactose, starch, etc., can be employed.

As the nitrogen source all the nitrogen compounds which are assimilable by yeasts, such as ammonium salts, amino acids, nitrate salts, etc., can be used.

The inorganic salts may include phosphates, magnesium salts, calcium salts, and a wide variety of other inorganic salts.

In any case, the carbon source or the nitrogen source may be of any type as long as it is assimilated by the yeast to be cultivated.

As a preferred culture medium the following can be given: ammonium sulphate gr 1.0; potassium phosphate basic gr 2.0; sodium phosphate dibasic gr 0.7; magnesium sulphate gr 0.5; yeast extract gr 1.0; glucose gr 20.0; tap water ml 1000. However, it is to be stressed that the concentration of the carbon or nitrogen source and the overall composition of the culture medium can vary depending upon the species or strain used on the adaptability of the yeast used for the production of "yeast rennet".

The temperature of cultivation will vary depending on the yeast used, even though the interval between 20° C. and 40° C. is considered suitable.

The cultivation is carried out, preferably in aerobic conditions, for 2–7 days, at pH 3.0–8.0, particularly at pH 4.5–6.0. The best results are obtained with an aerated liquid culture.

As a consequence of the above described cultivation, the milk-clotting enzyme denominated "yeast rennet" is produced in aerated liquid culture.

In order to obtain the enzyme containing solution which is to be subjected to subsequent purifying treatment, centrifugation or filtration are resorted to in order to separate the solids (yeast cells).

The "yeast rennet" enzyme contained in the solution thus deprived of solids, can then be concentrated or obtained in solid form by means of treatments such as precipitations with organic solvents, salting-out, concentration under low pressure, purification with ion exchangers, etc . . . As precipitating agents, organic solvents miscible with water such as methanol, isopropanol, acetone, ethanol, etc. can be used. All the salts that dissolve readily in water, such as ammonium sulphate, sodium chloride, magnesium sulphate, etc. can be used for salting-out.

The flacky and viscous precipitate obtained by means of any of the above mentioned procedures, is separated by decantation, resuspended in a small amount of deionized water and is freeze-dried.

Further purification can be achieved by dissolving the freeze-dried powder in water and dialyzing against water. The non-dialyzable portion is then freeze-dried and the final dry product has a milk-clotting activity of about 140 rennet units (R.U.) per milligram.

The "yeast or Blastomycetal rennet", the novel milk coagulating enzyme according to this invention, exhibits properties which are clearly and decidedly different from those of known proteases, whether animal, vegetal, or microbial in origin.

"Yeast rennet" shows a high coagulating activity, comparable to that of rennin and other microbial rennets, but its proteolytic activity is very weak likewise as in the instance of rennin. Moreover, as in the case of animal rennet obtained from the fourth stomach of sucking calves, its coagulating activity reaches its maximum at acid pH and remains constant as the pH rises to 7.0.

When its protease activity is determined according to the method of Sternberg in comparison to animal rennet, the absorbancy at 280 millimicrons was 0.060 (O.D.) for calf rennet and 0.078 (O.D.) for "yeast rennet". This indicates that the milk-clotting enzyme "yeast rennet" according to the invention is a completely different type of enzyme than the commonly used proteases of microbial origin.

The following examples are given in order to more clearly illustrate the product and the applications of the invention. It is to be understood that the examples are not limiting in any manner, being possible any changes as to the yeast species employed, the culture medium, the method of purification, etc., without departing from the scope of the invention.

EXAMPLE 1

A culture medium containing 0.1% of ammonium sulphate; 0.05% of magnesium sulphate; 0.2% of potassium phosphate monobasic; 0.07% of sodium phosphate dibasic; 0.1% of yeast extract; 2.0% of glucose, following 20 minutes sterilization at 115° C., was inoculated with a strain of *Criptococcus albidus* var. *aerius* and incubated at 28° C. After 72 hours of shaking culture, when the milk-clotting activity reached its peak, the yeast mass was separated from the broth by means of centrifugation. The enzyme activity of the supernatant was of ca. 80 Soxhlet units /ml, in connection with a 10% solution of skim powder milk containing 0.01 M of calcium chloride. After precipitation with ammonium sulphate, almost all the activity of the supernatant was transferred into the precipitate. By using organic solvents (ethanol 70%; methanol 70%; acetone 60%; isopropanol 65%) as precipitating agents, ca. 80% of activity could be recovered. The precipitate was resuspended in water, dialyzed against water and liophilized. The activity of the powder thus obtained was of ca. 140 rennet units (R.U.)/mg. This "yeast rennet" was then used to make "parmesan" type cheese. Namely, 100 liters of partially skimmed milk were inoculated with 2 liters of starter from the previous day processing. The whole was heated to 32.5° C. and 2 grams of yeast rennet were added. After 13–16 minutes the curd was formed and immediately overturned. After 5 additional minutes standing the whey became greenish and cutting was performed. The first cooking was carried out at 42° C. for 15 minutes, then the second at 54° C. for 15 minutes. After 10 minutes standing the whey was drained and the curd put into the press. A yield of 6–7% of parmesan cheese was thus obtained.

EXAMPLE 2

A culture medium containing 5% of powdered skim milk, 2% of glucose and 0.1% of yeast extract was inoculated with *Cryptococcus albidus* var. *aerius*. After 3 days of aerated culture at 28° C., the enzyme solution obtained after filtration of the culture broth showed a coagulating activity of ca. 100 rennet units (R.U.)/ml. By means of the purification procedure of Example 1, a powder characterized by an activity of 138 R.U./mg was obtained. A "caciotta" type cheese was then made with a yield of 12% after 24 hours.

EXAMPLE 3

A culture medium as in Example 2 was inoculated with a strain of *Cryptococcus albidus* and aerated for 4 days at 25° C. The supernatant of the culture thus obtained had a coagulating activity of 70 R.U./ml. With the freeze-dried powder obtained as in Example 1, parmesan cheese was made.

EXAMPLE 4

A *Candida lipolytica* strain was grown under agitation for 5 days at 28° C. on a medium containing molasses. 36 rennet units (R.U.)/ml were obtained in the supernatant. The cheese obtained proved quite normal.

EXAMPLE 5

The same culture conditions as in Example 2 were used for growing *Cryptococcus albidus* var. *diffluens* whereby a coagulating activity of ca. 16 rennet units (R.U.)/ml was formed in the supernatant.

EXAMPLE 6

The same medium as in Example 2 was inoculated with a strain *Rhodotorula glutinis* and an activity of 20 R.U./ml observed in the medium. After 4 days the culture broth was treated as in Example 4 whereby was obtained an enzyme solution showing an activity of ca. 20 rennet units (R.U.)/ml.

The invention herein is susceptible to numerous variations and modifications thereof, all of which fall within the scope of the instant inventive concept.

We claim:

1. A method for preparing a milk coagulating enzyme, comprising the steps of cultivating a yeast selected from the group consisting of *Cryptococcus albidus* species and variants thereof, on a nutrient medium containing at least one assimilable carbon source, at least one source of assimilable nitrogen and inorganic salts, to recover a culture broth containing a substance having a prevailing milk clotting activity and a comparatively low proteolytic activity, and extracting said substance from said culture liquid.

2. A method according to claim 1, wherein said yeast is selected from the *aerius* and *diffluens* variants of *Cryptococcus albidus* species.

3. A method according to claim 1, wherein the yeast cultivation is performed under aerobic conditions.

4. A method according to claim 1, wherein said cultivation is carried out at a temperature in the range of from about 15° C. to 40° C.

* * * * *